(12) United States Patent
Chen

(10) Patent No.: US 7,337,072 B2
(45) Date of Patent: Feb. 26, 2008

(54) FLUID SAMPLE TESTING SYSTEM

(75) Inventor: Shuqi Chen, Brookline, MA (US)

(73) Assignee: Chen & Chen, LLC, Framingham, MA (US)

( * ) Notice: Subject to any disclaimer, the term of this patent is extended or adjusted under 35 U.S.C. 154(b) by 592 days.

(21) Appl. No.: 10/863,603

(22) Filed: Jun. 8, 2004

(65) Prior Publication Data

US 2004/0223878 A1 Nov. 11, 2004

Related U.S. Application Data

(63) Continuation of application No. 09/910,233, filed on Jul. 20, 2001, now Pat. No. 6,748,332, which is a continuation of application No. 09/339,056, filed on Jun. 23, 1999, now Pat. No. 6,318,191.

(60) Provisional application No. 60/090,471, filed on Jun. 24, 1998.

(51) Int. Cl.
*C12M 1/00* (2006.01)
*G01N 33/50* (2006.01)

(52) U.S. Cl. .................. 702/19; 435/283.1; 436/8; 436/53

(58) Field of Classification Search .................. 702/19
See application file for complete search history.

(56) References Cited

U.S. PATENT DOCUMENTS 3,036,894 A 5/1962 Forestiere

| | | |
|---|---|---|
| 3,441,205 A | 4/1969 | Young, Jr. |
| 3,579,303 A | 5/1971 | Pickering |
| 3,607,097 A | 9/1971 | Auphan et al. |
| 3,620,678 A | 11/1971 | Gulgan et al. |
| 3,698,822 A | 10/1972 | Polanyi |

(Continued)

FOREIGN PATENT DOCUMENTS

DE 2 007 405 10/1970

(Continued)

OTHER PUBLICATIONS

Chen, et al., "Enhanced aggregability of red blood cells of β-thalassemia major patients," Am. Physiol. Soc., H1951-1956 (1996).

(Continued)

*Primary Examiner*—John Barlow
*Assistant Examiner*—Jonathan Moffat
(74) *Attorney, Agent, or Firm*—Scott E. Kamholz; Foley Hoag, LLP

(57) ABSTRACT

A sample testing system may include a housing, a cavity in the housing to receive a chamber, two contact members, and a sensor. The contact members may be positioned to be engageable with respective portions of the chamber inserted in the cavity, and to compress those respective portions, thereby driving fluid flow. A sample testing system may include a housing, a cavity in the housing to receive a chamber, at least one contact member, and a sensor. The at least one contact member may be positioned to be engageable with a first segment of the chamber when the chamber is in the cavity, and to compress the first segment, thereby defining a gap of the first segment of the chamber and a reservoir in at least a second segment of the chamber.

22 Claims, 10 Drawing Sheets

U.S. PATENT DOCUMENTS

| | | | |
|---|---|---|---|
| 3,918,913 A | | 11/1975 | Stevenson et al. |
| 4,065,263 A | | 12/1977 | Woodbridge, III |
| RE29,725 E | | 8/1978 | Johnson et al. |
| 4,166,457 A | | 9/1979 | Jacobsen et al. |
| 4,187,861 A | | 2/1980 | Heffernan |
| 4,267,149 A | | 5/1981 | Bruckner et al. |
| 4,329,698 A | | 5/1982 | Smith |
| 4,426,451 A | | 1/1984 | Columbus |
| 4,596,271 A | | 6/1986 | Brundage |
| 4,695,430 A | | 9/1987 | Coville et al. |
| 4,752,449 A | | 6/1988 | Jackson et al. |
| 4,820,297 A | | 4/1989 | Kaufman et al. |
| 4,822,568 A | * | 4/1989 | Tomita ................ 422/73 |
| 4,846,005 A | | 7/1989 | Bacehowski et al. |
| 4,900,321 A | | 2/1990 | Kaufman et al. |
| 4,917,864 A | | 4/1990 | Marsoner et al. |
| 5,061,445 A | | 10/1991 | Zoski et al. |
| 5,087,425 A | | 2/1992 | Flossdorf et al. |
| 5,143,084 A | | 9/1992 | Macemon et al. |
| 5,176,203 A | | 1/1993 | Larzul |
| 5,229,297 A | | 7/1993 | Schnipelsky et al. |
| 5,244,813 A | | 9/1993 | Walt et al. |
| 5,374,395 A | | 12/1994 | Robinson et al. |
| 5,380,665 A | * | 1/1995 | Cusack et al. ............ 436/53 |
| 5,422,271 A | | 6/1995 | Chen et al. |
| 5,455,175 A | | 10/1995 | Wittwer et al. |
| 5,475,610 A | | 12/1995 | Atwood et al. |
| 5,491,067 A | | 2/1996 | Setcavage et al. |
| 5,504,007 A | | 4/1996 | Haynes |
| 5,508,197 A | | 4/1996 | Hansen et al. |
| 5,576,218 A | | 11/1996 | Zurek et al. |
| 5,591,573 A | | 1/1997 | Whalen et al. |
| 5,602,756 A | | 2/1997 | Atwood et al. |
| 5,626,732 A | * | 5/1997 | Allington ................ 204/453 |
| 5,631,683 A | | 5/1997 | Nishioka et al. |
| 5,656,501 A | | 8/1997 | Yedgar et al. |
| 5,668,330 A | | 9/1997 | Bartlett-Hooker et al. |
| 5,709,668 A | | 1/1998 | Wacks |
| 5,735,824 A | | 4/1998 | Hjertman |
| 5,780,222 A | | 7/1998 | Peddada et al. |
| 5,795,547 A | | 8/1998 | Moser et al. |
| 5,801,052 A | | 9/1998 | Bartlett-Hooker et al. |
| 5,810,778 A | | 9/1998 | Hjertman |
| 5,830,411 A | | 11/1998 | Martinell Gisper-Sauch |
| 5,847,734 A | | 12/1998 | Pawlowski, Jr. |
| 5,897,842 A | | 4/1999 | Dunn et al. |
| 5,942,432 A | | 8/1999 | Smith et al. |
| 5,985,651 A | | 11/1999 | Hunicke-Smith |
| 6,016,683 A | | 1/2000 | Betts et al. |
| 6,019,945 A | | 2/2000 | Ohishi et al. |
| 6,033,880 A | | 3/2000 | Haff et al. |
| 6,066,296 A | | 5/2000 | Brady et al. |
| 6,163,714 A | | 12/2000 | Stanley et al. |
| 6,186,982 B1 | | 2/2001 | Gross et al. |
| 6,194,160 B1 | | 2/2001 | Levin |
| 6,210,369 B1 | | 4/2001 | Wilmot et al. |
| 6,251,660 B1 | | 6/2001 | Muir et al. |
| 6,299,601 B1 | | 10/2001 | Hjertman |
| 6,303,083 B1 | | 10/2001 | Johnson et al. |
| 6,440,725 B1 | | 8/2002 | Purahmadi et al. |
| 2003/0208105 A1 | * | 11/2003 | Newman et al. ............ 600/300 |

FOREIGN PATENT DOCUMENTS

| | | |
|---|---|---|
| DE | 27 53 865 | 6/1979 |
| EP | 0 047806 | 3/1982 |
| EP | 0 435 380 A | 3/1991 |
| EP | 0488769 A2 | 11/1991 |
| EP | 0504772 A2 | 9/1992 |
| EP | 0739241 B1 | 8/1998 |
| EP | 0955097 A1 | 11/1999 |
| EP | 1000661 A1 | 5/2000 |
| EP | 1 106 250 A2 | 6/2001 |
| FR | 1 513 306 | 5/1968 |
| FR | 2590673 | 5/1987 |
| FR | 2672231 | 8/1992 |
| WO | WO 97/27324 | 7/1997 |
| WO | WO 97/40939 | 11/1997 |
| WO | WO 97/48818 | 12/1997 |
| WO | WO 98/43740 | 10/1998 |
| WO | WO 98/50147 | 11/1998 |
| WO | WO 99/26724 | 6/1999 |
| WO | WO 99/67646 | 12/1999 |
| WO | WO 00/13014 | 3/2000 |
| WO | WO 00/25920 | 5/2000 |

OTHER PUBLICATIONS

Chen, et al., "Rolling and transient tethering of leukocytes on antibodies reveal specializations of selectins," Proc. Natl. Acad. Sci. USA 94:3172-3177 (1997).

Taylor, et al., "Enhanced Human Red Blood Cell Aggregation While Diving," Naval Medical Research Institute, Bethesda, MD and Dept. of Biochemistry, Hebrew University-Hadasseh Medical School, Jerusalem, Israel (1997).

Alon, et al, "The Kinetics of L-selectin Tethers and the Mechanics of Selectin-mediated Rolling,", *J. Cell Biol.*, 138 (5); 1169-1180 (1997).

Ben-Hur et al., "Photodynamic Treatment of Red Blood Cell Concentrates for Virus Inactivation Enhances Red Blood Cell Aggregation: Protection with Antioxidants," *Photochem. and Photobiol.*, 66(4):509-512 (1997).

Chen et al, "Monitoring of Red Blood Cell Aggregability in a Flow-Chamber by Computerized Image Analysis," *Clin. Hemorheology*, 14(4): 497-507 (1994).

Chen, et al., "Red blood cell aggregability is enhanced by physiological levels of hydrostatic pressure", *Biochimica et Biophysica Acta 1192*, Elsevier Science B.V., 247-252 (1994).

Chen, et al., "Monitoring of Erythrocyte Aggregate Morphology Under Flow by Computerized Image Analysis," Biorheology, 32(4):498-496 (1995).

Kenneth Mason Publications; "Simplified PCT Processor and Method", Research Disclosure, Hampshire, GB, vol. 401, pp. 651-655, (Sep. 1, 1997).

Kenneth Mason Publications; "PCR Processor", Research Disclosure, Hampshire, GB, vol. 396 pp. 207-211, (Apr. 1, 1997).

International Search Report Completed on Jun. 27, 2002 and Mailed on Jul. 16, 2002.

Partial International Search Report Mailed on Jul. 8, 2003.

* cited by examiner

FLUID SAMPLE TESTING SYSTEM

CROSS-REFERENCE TO RELATED APPLICATIONS

This application is a continuation of application Ser. No. 09/910,233, filed Jul. 20, 2001, now U.S. Pat. No. 6,748,332, which is a continuation of application Ser. No. 09/339,056, filed Jun. 23, 1999, now U.S. Pat. No. 6,318,191, which claims the benefit of U.S. Provisional Application No. 60/090,471, filed Jun. 24, 1998. Each of the aforementioned applications is hereby incorporated herein by this reference.

INTRODUCTION

The present invention is directed to a system for testing a fluid sample, and, more particularly, to a fluid sample testing system having improved automation, safety and efficiency.

BACKGROUND

Collection, transportation and pretreatment of fluid samples, such as blood samples, are currently done generally in a manual fashion. Blood is commonly collected in test tubes and samples from these test tubes are deposited in reaction chambers for testing. These tubes can be placed in an automated testing machine to perform testing using various assays. This process can be expensive, time consuming, and may lead to human error, possibly leading to false test results. Current automated testing systems require large capital investment; incur high costs for reagents, disposables, operation, maintenance, service and training; and do not provide required sample pretreatment.

It is an object of the present invention to provide a sample testing system which reduces or wholly overcomes some or all of the aforesaid difficulties inherent in prior known devices. Particular objects and advantages of the invention will be apparent to those skilled in the art, that is, those who are knowledgeable or experienced in this field of technology, in view of the following disclosure of the invention and detailed description of certain preferred embodiments.

SUMMARY

The principles of the invention may be used to advantage to provide a sample testing system which is highly automated, thereby increasing efficiency, reducing costs, and increasing safety due to reduced handling of samples. A sample can be collected in a chamber which is then divided into a plurality of sealed segments. A reagent can be added to a segment and the segment can be inspected to detect a condition of the sample.

In accordance with a first aspect, a sample testing system has a chamber sealing apparatus to form a plurality of seals defining a plurality of fluid-tight segments of the chamber. A reagent injector cartridge actuator is adapted to receive a reagent injector cartridge having at least one needle in fluid communication with a reagent reservoir, and to move a reagent injector cartridge to inject a quantity of reagent into a segment of a chamber. A sensor generates an output signal corresponding to a condition of a fluid sample material within a segment of a chamber.

In accordance with another aspect, a sample testing system has a tube sealing apparatus having a tube compression and sealing member to laterally seal a flexible plastic tube containing a fluid sample material, whereby a fluid-tight tubule containing a portion of the fluid sample material can be formed between axially spaced lateral seals. A reagent injector cartridge actuator is adapted to receive a reagent injector cartridge having at least one needle in fluid communication with a reagent reservoir, and to move a reagent injector cartridge to inject a quantity of reagent into a tubule. A flow control device has a contact member movable into contact with a tubule to effect mechanically induced fluid flow within a fluid passageway in the tubule. An inspection system has a light detector to receive light passed through a tubule and to generate an output signal corresponding to a condition of the fluid sample material within a tubule.

In accordance with another aspect, a sample testing system has a tube sealing apparatus having a tube compression and sealing member to laterally seal a flexible plastic tube containing a fluid sample material, whereby a fluid-tight tubule containing a portion of the fluid sample material can be formed between axially spaced lateral seals. A reagent injector has at least one needle in fluid communication with a reagent reservoir, and a needle actuator to insert the needle into a tubule and inject a quantity of reagent into a tubule. A flow control device has a contact member movable into contact with a tubule to effect mechanically induced fluid flow within a fluid passageway in the tubule. An inspection system has a light detector to receive light passed through a tubule and to generate an output signal corresponding to a condition of the fluid sample material within a tubule.

In accordance with another aspect, a reagent cartridge has a housing and at least one reservoir in the housing. At least one needle in the housing is in fluid communication with one of the reagent reservoirs. A needle actuator inserts the needle into a tubule and injects a quantity of reagent.

In accordance with yet another aspect, a sample testing tubule has a length of flexible plastic tube having fluid-tight lateral seals at axially spaced locations to define a fluid-tight fluid sample chamber between the lateral seals containing a fluid sample material. A self-sealing injection channel is formed in the tubule, the injection channel being normally substantially free of fluid sample material and capable of fluid communication with the fluid sample material in the tubule.

In accordance with another aspect, a method of performing a sample assay includes the following steps: collecting a sample of fluid material into a length of substantially transparent, flexible, heat-sealable, plastic tube; inserting the tube into a sample testing machine having a tube sealing apparatus, a reagent injector having at least one needle in fluid communication with a reagent reservoir and a needle actuator to insert the needle into a tubule and inject a quantity of reagent, a flow control device having a contact member movable into contact with a tubule to effect mechanically induced fluid flow within the tubule, and an inspection system having a light detector to receive light passed through a tubule and to generate an output signal corresponding to a condition of the sample material within a tubule; actuating the tube sealing apparatus to seal lengths of the tube into tubules; actuating the needle actuator to insert the needle into a selected tubule and inject reagent to form a mixture of sample material and reagent in the selected tubule; actuating the flow control device to mix the mixture of sample material and reagent; and actuating the inspection system to inspect the mixture and to generate an output signal corresponding to a condition of the mixture.

From the foregoing disclosure, it will be readily apparent to those skilled in the art, that is, those who are knowledgeable or experienced in this area of technology, that the present invention provides a significant technological advance. Preferred embodiments of the fluid sample testing system of the present invention can provide increased efficiency, reduced costs, and increase safety. These and additional features and advantages of the invention disclosed here will be further understood from the following detailed disclosure of certain preferred embodiments.

BRIEF DESCRIPTION OF THE DRAWINGS

Certain preferred embodiments are described in detail below with reference to the appended drawings wherein.

Figure 1:
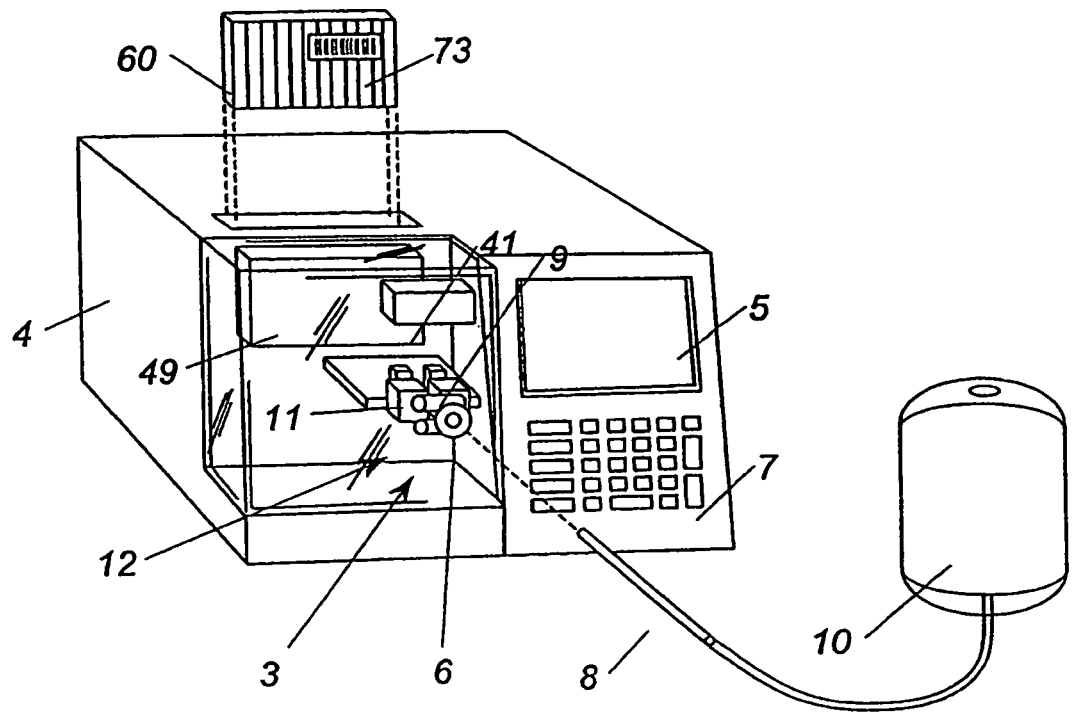
FIG. 1 is a partially schematic perspective view of a sample testing system in accordance with a preferred embodiment of the present invention.

The figures referred to above are not drawn necessarily to scale and should be understood to present a representation of the invention, illustrative of the principles involved. Some features of the sample testing system depicted in the drawings have been enlarged or distorted relative to others to facilitate explanation and understanding. The same reference numbers are used in the drawings for similar or identical components and features shown in various alternative embodiments. Sample testing system as disclosed herein, will have configurations and components determined, in part, by the intended application and environment in which they are used.

DETAILED DESCRIPTION OF CERTAIN PREFERRED EMBODIMENTS

The present invention has many uses which will become readily apparent to those skilled in the art, given the benefit of this disclosure. Sample material to tested may be, e.g., blood, cell suspensions, biofluids or other fluids. Exemplary tests to be performed on fluid samples include clinical diagnosis, therapeutic monitoring, and screening of chemical compounds for discovery of new drugs. The following discussion will discuss blood testing specifically for purposes of illustration.

The present invention provides for a chamber containing a fluid sample to be divided into a plurality of segments, with fluid-tight seals separating adjacent segments from one another. It is considered to be a highly advantageous feature of certain preferred embodiments that a chamber into which a fluid sample is drawn, e.g., a tube into which a patient's blood is drawn, can itself then also be the testing or reaction chamber within which that blood or other fluid sample is tested, without ever having to remove the blood or fluid sample from the chamber.

Referring to FIG. 1, a testing machine according to the present invention is shown generally by the reference numeral 2. Testing machine 2 comprises a housing 4 having an entry port 6 on a front side thereof for receiving a chamber containing a fluid sample. The chamber is received in a cavity in the housing, so sized and shaped to receive the chamber. In the illustrated embodiment, the chamber is a tube 8 from a blood bag 10. Tube 8 is preferably a flexible, thermoplastic, substantially transparent tube having an inner diameter of approximately 1 mm to 5 mm, preferably approximately 3-4 mm. Tube 8 may be formed of polyvinylchloride (PVC) or other suitable material. A control panel 7 is located on the front of housing 4 to receive information, such as information read from bar code labels or keyed data, and a monitor 5 displays operating information, such as the results of testing. A tube sealing apparatus 12, described in greater detail below, is contained within housing 4 for sealing portions of tube 8 into tubules 14. Reagent cartridge 60 is loaded into a reagent cartridge actuator 49 in housing 4, with reagent from reservoirs 16 contained within reagent cartridge 60 being added to tubules 14 (described in greater detail below). A sensor 41 in housing 4 reads a bar code label 73 (seen in FIG. 22) on reagent cartridge 60 which provides information identifying the particular reagent or reagents in reagent cartridge 60 as well as information regarding test procedures associated with the particular reagent or reagents. Mixing device or flow control device 18, seen in FIG. 2 and described in greater detail below, is also contained within housing 4 for creating a fluid passageway to allow the flow of cells within tubule 14. Computerized microscopic inspection system 20 is mounted in housing 4 to view and analyze the flow of cells within tubule 14. In certain preferred embodiments, multiple testing machines 2 may be connected to computer analysis and system control components of inspection system 20, either directly, or via a computer network. In certain preferred embodiments, flow control device 18 may not be present, or may not be employed if present. In such an alternative embodiment, inspection system 20 inspects a sample within tubule 14 without a flow of cells within the sample being created.

A tube advancement system 3 is provided to support and control forward movement of tube 8 through testing machine 2. Suitable tube advancement systems will become readily apparent to those skilled in the art, given the benefit of this disclosure. In the embodiment illustrated in FIG. 2, tube advancement system 3 comprises a pair of rotating wheels 22 which rotate in opposite directions to advance the tube. At least one wheel 22 is connected to and driven by output shaft 23 of a motor which is not shown. Tube 8 is inserted between rotating wheels 22 and advanced into tube sealing apparatus 12. The volume of sample within each tubule 14 is controlled by compressing tube 8. Specifically, upper plunger 9 and lower plunger 11 are spaced apart from one another and movable toward one another to partially compress a tubule 14 positioned therebetween prior to it being sealed. An upper, or first sealing head 24 and a lower, or second sealing head 26 compress a portion of tube 8 and then use radio frequency energy to seal tube 8, forming lateral seals 13 between adjacent tubules 14. Lateral seals, as used herein, refer to seals which separate axially adjacent portions of tube 8. In a preferred embodiment, the lateral seals extend substantially perpendicular to a longitudinal axis of tube 8. Seals 13 are fluid-tight seals, that is, seals 13, under normal operating conditions, prevent the flow of fluid through the seal. Each tubule 14 contains a sample of blood. The length of each tubule 14 is preferably approximately 3 to 15 mm, and more preferably about 5 to 10 mm. Reagent is added to tubule 14 via needle 15 of injector 17.

Tubules 14 then advance to one of an incubation chamber 19, a centrifuge 35, or flow control device 18. Flow control device 18 forms a pair of reservoir zones in tubule 14 with a thin fluid passageway extending between the reservoirs. Light from light source 28 is projected through the tubule 14 in flow control device 18. A camera with a microscopic lens 30 captures images of blood cell aggregates flowing from one reservoir zone to the other through the thin passageway. It sends the images to a frame grabber 32, which in turn sends the images to programmable control system or computer 34 for analysis. The results of the testing done in computer 34 may be transmitted to display 7, seen in FIG. 1, for reading by an operator. In other preferred embodiments, the results of the testing may be stored for later retrieval, or forwarded to another computer or other device, e.g. a printer for preparing a hard copy of the results.

Centrifuge 35 is provided to separate components of the sample in a length of tube 8 in a known fashion. A length of tube 8, typically longer than a typical tubule 14, is conveyed to centrifuge 35 via suitable conveying means. Once the components of the sample in the length of tube 8 have been separated, the length of tube is sealed into tubules 14 providing a fluid-tight seal between the different components. The length of tube is sealed either by a tube sealing apparatus at centrifuge 35, or it may be advanced to tube sealer 12 by suitable conveying means for sealing. Centrifuge 35 may also be used during testing in order to perform certain assays.

In certain preferred embodiments, selected tubules 14 may be stored in incubation chamber 19 prior to advancing to flow control device 18. Incubation chamber 19 may provide temperature control of tubules 14, and may allow the addition of a second reagent to tubules 14. Temperature controlling means 21 is connected to incubation chamber 19 to heat and/or cool incubation chamber 19. It is to be appreciated that the temperature of tubules 14 may be controlled directly, such as with a temperature sensor detecting the temperature of tubules 14 and maintaining a desired setpoint temperature. Alternatively, the temperature of the tubules could be controlled indirectly by sensing and controlling the temperature of incubation chamber 19. Temperature controlling means 21 may include a heating element and may also include a cooling device. Other suitable temperature controlling means will become readily apparent to those skilled in the art given the benefit of this disclosure.

Figure 3:
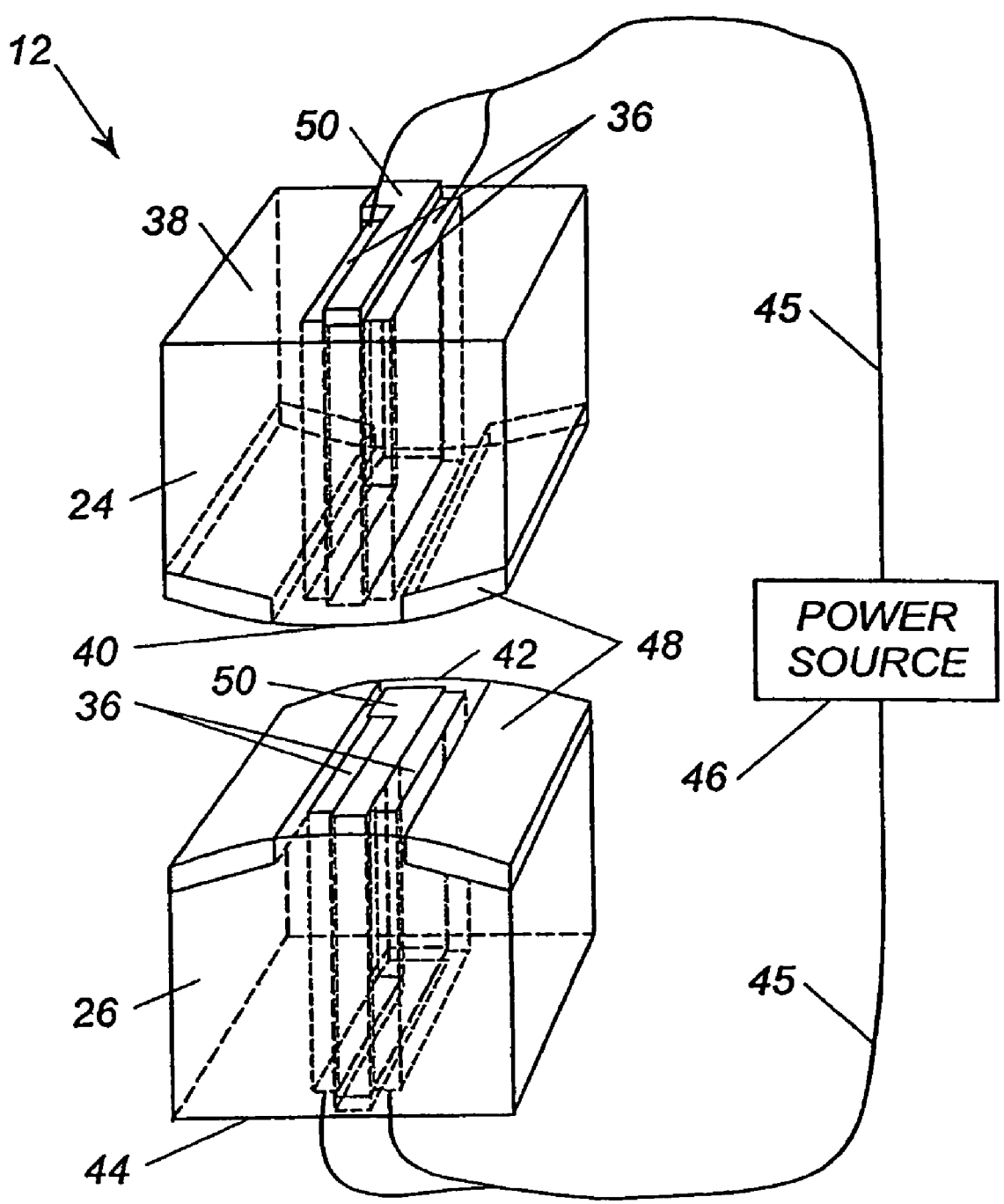
FIG. 3 is a schematic perspective view, partially in phantom, of a tube sealing apparatus of the testing system of FIG. 1.
Figure 4:
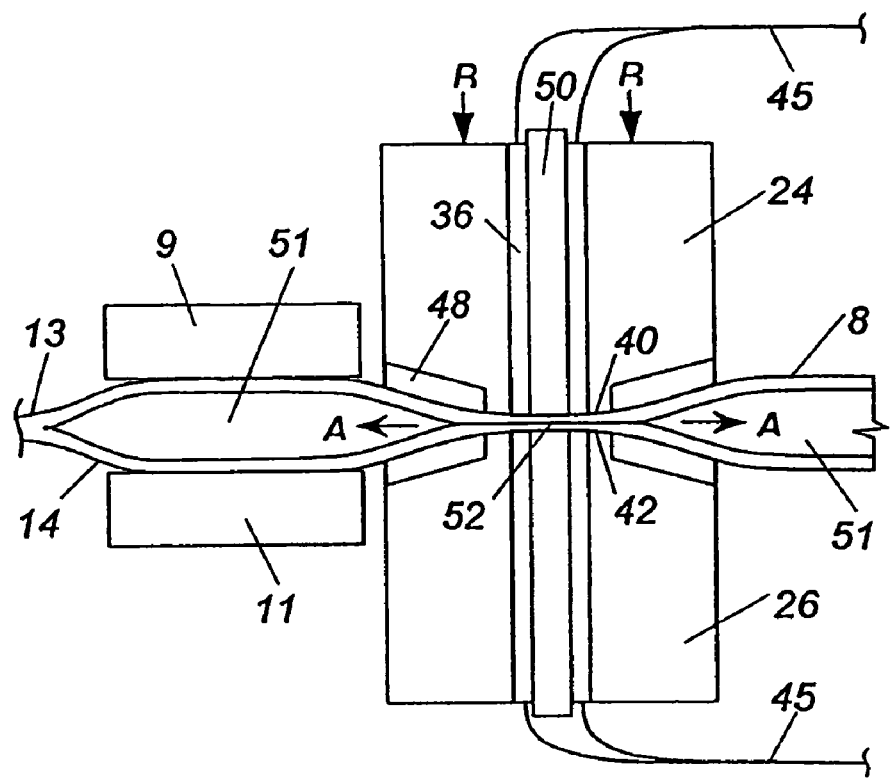
FIG. 4 is a schematic elevation view, shown partially cut away, of a tube being compressed by the tube sealing apparatus of FIG. 3.

Turning now to FIG. 3, tube sealing apparatus 12 will be shown in greater detail. Tube sealing apparatus 12 comprises upper, or first sealing head 24 and lower, or second sealing head 26. Upper sealing head 24 has conductors 36 extending from an upper surface 38 to a lower sealing surface 40. Lower sealing head 26 also has conductors 36 extending from an upper sealing surface 42 to a lower surface 44. Conductors 36 are connected by cables 45 to a power source 46 which creates a radio frequency (RF) electrical field between the conductors 36 of upper sealing head 24 and lower sealing head 26 which heat seals tube 8. Conductors 36 are preferably formed of a material having high electrical and heat conductivity. Suitable materials for conductor 36 are, for example, metals such as copper. Other suitable materials for the sealing heads will become readily apparent to those skilled in the art, given the benefit of this disclosure. Upper sealing head 24 and lower sealing head 26 are preferably formed of a substantially rigid insulating material having high heat conductivity. Suitable materials for the sealing heads include plastics such as nylon. Other suitable materials for the sealing heads will become readily apparent to those skilled in the art, given the benefit of this disclosure. Resilient pads 48 are preferably located at the outer edges of lower sealing surface 40 and upper sealing surface 42. Resilient pads 48 may be formed of rubber, silicone rubbers, teflon, fluoropolymers, or any other suitable resilient material. In certain preferred embodiments, a central bar 50 may be located between a pair of conductors 36. As seen in FIG. 4, both upper sealing head 24 and lower sealing head 26 have a central bar 50. It is to be appreciated that in certain preferred embodiments, only upper sealing head 24 may have a central bar 50, while lower sealing head 26 has a single conductor 36.

As seen in FIG. 4, tube 8, containing fluid sample 51, e.g., whole blood, is passed between upper sealing head 24 and lower sealing head 26. The volume of a portion of tube 8, or tubule 14, is adjusted by compressing upper bar 9 and lower bar 11 together about tubule 14. In certain preferred embodiments, the volume of tubule 14 is approximately 20 µl. The tubule 14 may contain, for example, approximately 5 µl of whole blood or approximately 15 μl of plasma. Upper and lower sealing heads 24, 26 are then squeezed together under pressure, compressing a portion of tube 8 and pushing fluid sample 51 outwardly in the direction of arrows A. As sealing heads 24, 26 compress tube 8, a sample free zone 52 is created, that is, a zone is created within tube 8 which is substantially free of any fluid sample 51. The pressure must be sufficient to squeeze fluid sample 51 out of sample free zone 52 as well as sufficient to prevent pressure in tubule 14 from forcing fluid sample 51 back into sample free zone 52, especially during sealing. The required pressure forcing sealing heads 24, 26 together is dependent on the material of tube 8, as well as its diameter and wall thickness. In certain preferred embodiments, fluid sample 51 is approximately 2 mm away from conductors 36 which provide the sealing of tubule 14.

Figure 5:
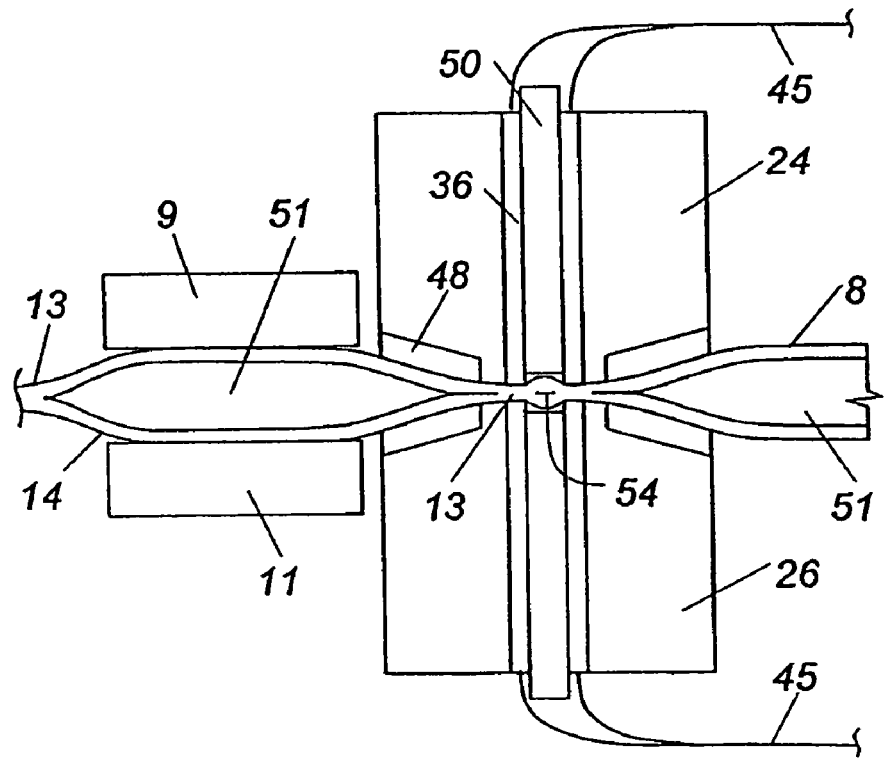
FIG. 5 is a schematic elevation view, shown partially cut away, of a tube being sealed by the tube sealing apparatus of FIG. 3.

As seen in FIG. 5, central bar 50 is then raised, releasing the pressure in a central area of sample free zone 52 and creating an injection channel 54 which is also free of fluid sample 51. Power source 46 then supplies RF power through cables 45 to conductors 36 which seals tube 8 forming seal 13. In certain preferred embodiments, the frequency of the RF power supplied is approximately 40 MHz. The RF power is supplied for a time period typically less than one second. The power and duration of the supplied RF energy may vary based on the size of tube 8 and the material of which it is constructed. Upper sealing member 24 is then raised, tube 8 is advanced to the left as seen in FIG. 4, and tube 8 is sealed again, forming a tubule 14 between seals 13. By creating sample free zone 52, fluid sample 51 is kept a safe distance from conductors 36 when the RF power is applied, thereby reducing negative effects on fluid sample 51 from the RF power and the heat it generates.

In the embodiment illustrated in FIG. 4, lower sealing head 26 is fixed and upper sealing head 24 moves downwardly in the direction of arrows B toward lower sealing head 26. In other preferred embodiments, upper sealing head 24 may be fixed with lower sealing head 26 moving toward upper sealing head 24, or both upper and lower sealing heads 24, 26 may move toward one another.

In the embodiment illustrated in FIGS. 4, 5, lower sealing surface 40 and upper sealing surface 42 have a substantially convex profile. Thus when sealing heads 24, 26 are brought together, tube 8 is compressed a maximum amount in the central area of heads 24, 26, that is, in sample free zone 52, and compresses to a lesser extent outside of sample free zone 52.

Figure 6:
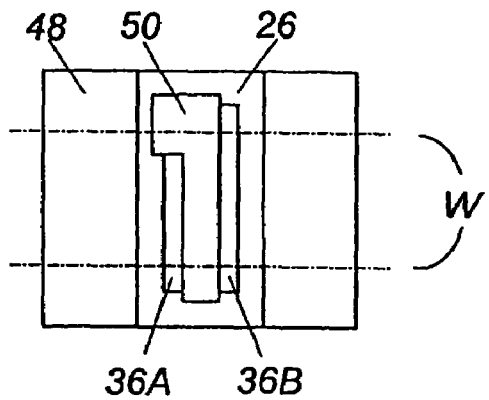
FIG. 6 is a schematic plan view of a sealing head of the tube sealing apparatus of FIG. 3.
Figure 7:
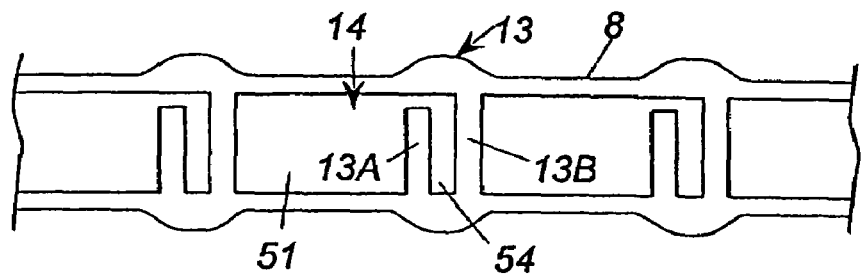
FIG. 7 is a schematic plan view of a plurality of tubules formed in a length of tube by the tube sealing apparatus of FIG. 3.

In certain preferred embodiments, as seen in FIG. 6, central bar 50 has an L shaped, or inverted L shaped profile. In the embodiment illustrated, central bar 50 of first sealing head 24 has an inverted L shape and central bar 50 of second sealing head 26 has an L shape. Conductor 36 is formed of conductor element 36A and conductor element 36B, spaced apart by central bar 50. Conductor element 36A extends along the long leg of central bar 50 and terminates at its short leg. Conductor element 36 B extends along the length of the long leg of central bar 50. Lines W represent the width of a tube 8 which is sealed by sealing heads 24, 26. It can be seen that the sealing heads extend beyond the edge of the tube such that the seal, when formed, extends across the entire width of the tube. When the RF power is applied, as seen in FIG. 7, seal 13, comprising first portion 13A and second portion 13B is formed only in the areas where conductor elements 36A, 36B lie, creating L shaped injection channel 54 which is capable of being in fluid communication with tubule 14. However, tension in the area of seal 13 prevents fluid sample 51 from entering injection channel 54. Reagent is added to injection channel 54 through needle 15, seen in FIG. 2 and described in greater detail below. The amount of reagent added to tubule 14 is preferably approximately 1-15 μl depending on the assay being performed. By maintaining injection channel 54 free of fluid sample 51, any leakage from tubule 14 is prevented when a needle punctures the side wall of the tube to inject reagent into the tubule through injection channel 54. In certain preferred embodiments, the needle puncture in injection channel 54 has been found to be able to withstand pressure of up to approximately 3 atm. without leaking.

The specific configuration of injection channel 54 is not critical, except that it must be sufficiently large to receive the reagent injection needle. Also, in accordance with a highly advantageous aspect, indicated above, it is sufficiently small so as to be self-sealing. That is, the bore, length, and configuration of the injection channel are such that the passageway is normally substantially devoid of fluid sample. Given the benefit of this disclosure of the general concept and principles of the injection channel, it will be within the ability of those skilled in the art to select suitable dimensions and configurations for the injection channel, taking into account the size, wall thickness and resiliency of the flexible plastic tube. Thus, while the injection channel is normally closed or collapsed so as to be devoid of fluid sample, it still provides fluid communication into the main fluid chamber within the tubule. That is, reagent or other fluid injected into the injection channel under suitable injection pressure passes through the injection channel to the main chamber. Once the injection needle is withdrawn, however, the injection channel returns to its closed or collapsed condition such that leakage does not occur during normal operating conditions through the hole in the wall formed at the end of the passageway by the needle.

Figure 8:
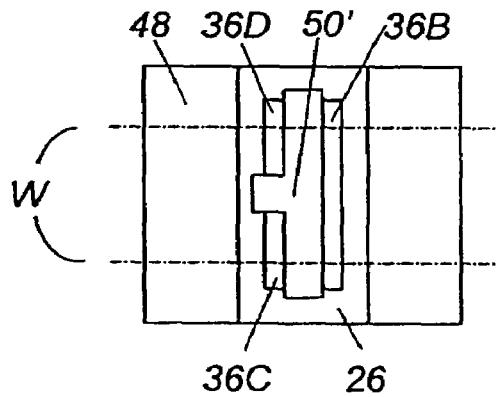
FIG. 8 is a schematic plan view of an alternative embodiment of a sealing head of the tube sealing apparatus of FIG. 3.
Figure 9:
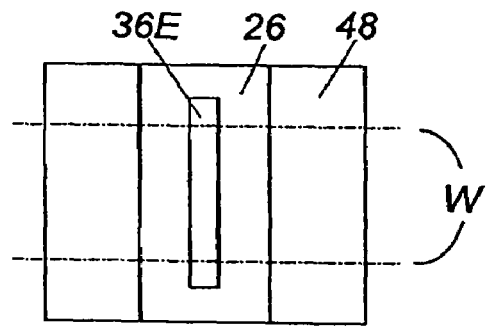
FIG. 9 is a schematic plan view of another alternative embodiment of a sealing head of the tube sealing apparatus of FIG. 3.

In another preferred embodiment, seen in FIG. 8, central bar 50' has a T shaped profile with conductor 36 comprising conductor elements 36B, 36C, and 36D. In yet another preferred embodiment, seen in FIG. 9, conductor 36 is formed of a single conductor element 36E. In this embodiment, a single lateral seal 13 is formed across tube 8. Alternatively, tube 8 or tube sealing apparatus 12 can be repositioned after a first seal 13A is formed, creating a second seal 13B as seen in FIG. 7 to form an injection channel 54.

Figure 2:
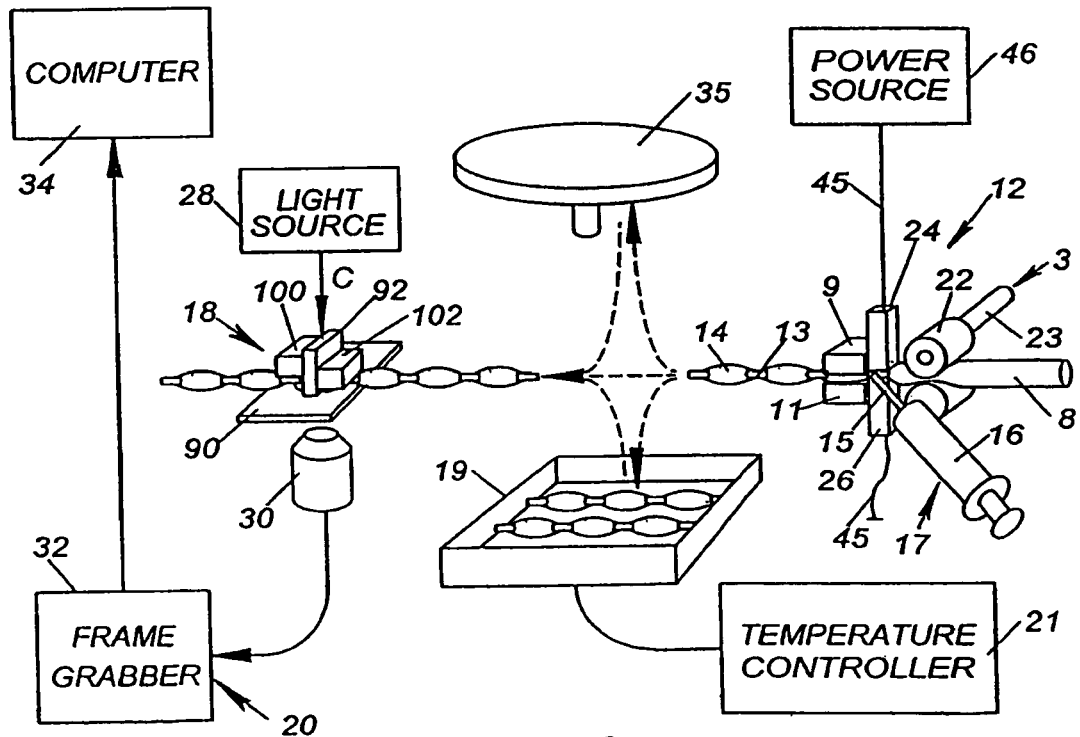
FIG. 2 is a schematic representation of the components of the sample testing system of FIG. 1.

As shown in FIG. 2, needle 15 is inserted into tubule 14, preferably into injection channel 54, to add reagent to fluid sample 51 into tubule 14. In a preferred embodiment, the reagent is added through injection channel 54 prior to upper and lower sealing heads 24, 26 being fully released. In other preferred embodiments, the reagent is added just prior to the tubule 14 entering flow control device 18, so that the inspection of the sample is done soon after the reagent has been added. Reagent can be drawn from reservoir 16 by releasing upper and lower bars 9, 11, creating vacuum pressure within tubule 14 and drawing reagent into tubule 14. Central bar 50 may then be depressed, forcing any reagent remaining in injection channel 54 into tubule 14.

Figure 24:
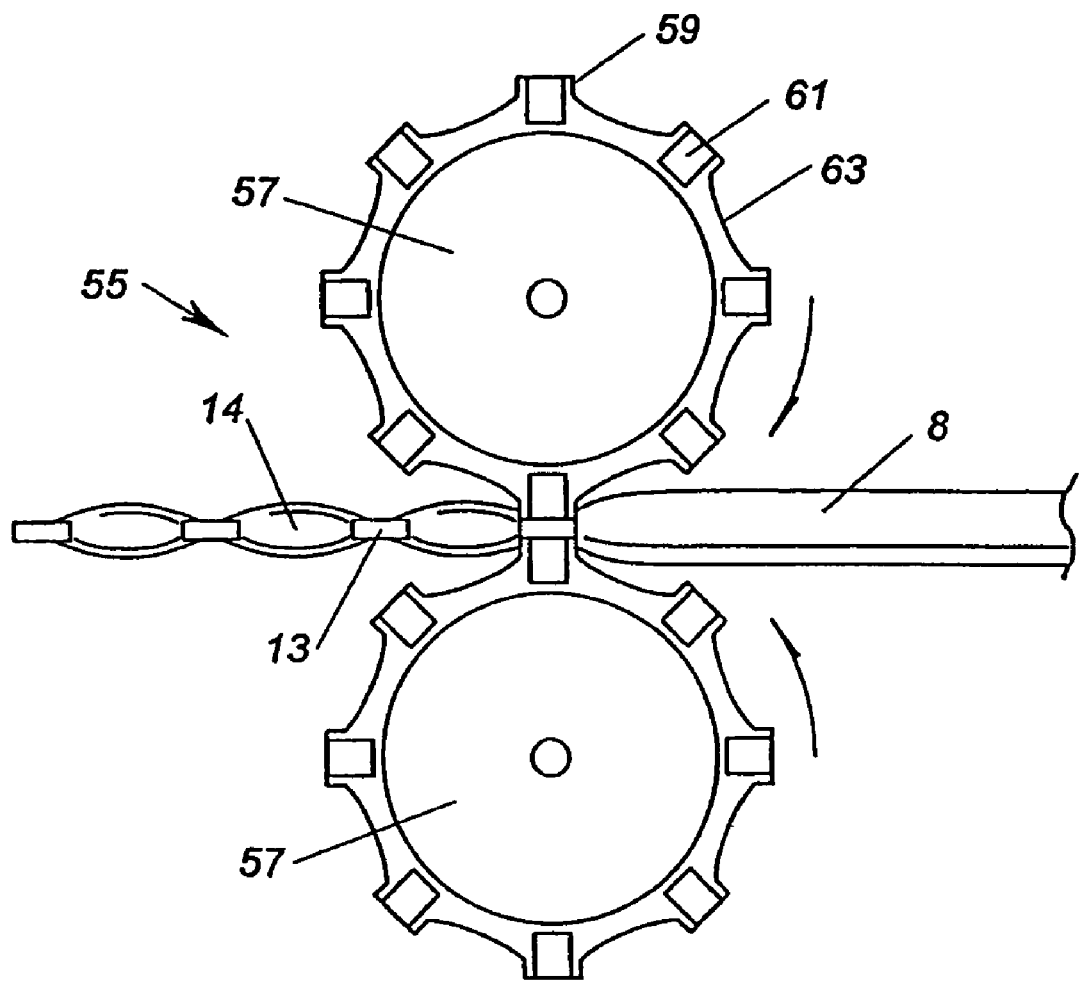
FIG. 24 is a schematic elevation view of an alternative embodiment of the tube sealing apparatus of FIG. 1.

As seen in FIG. 24, tube sealing apparatus 55 may comprise a pair of rotatable wheels 57 having a plurality of circumferentially disposed teeth 59. The outer surface of each tooth 59 is substantially planar or curvoplanar. A conductor 61 operably connected to power source 46 by cables (not shown) is located within each tooth 59. The surface 63 of wheels 57 extending between teeth 59 is substantially concave. Wheels 57 rotate in opposite directions to progress tube 8 through tube sealing apparatus 55, with surfaces 63 preferably being configured to compress each portion of tube 8 between the seals to a desired volume. As an opposed pair of teeth 59 meet, radio frequency energy or heat, etc. is transmitted through conductors 61, forming seal 13 in the manner described above.

In other preferred embodiments, sealing of the chamber or tube 8 can be accomplished by other suitable sealing means. Examples of other sealing means include, for example, mechanical clamps, a fold lock, ultrasound fusion, and direct application of heat to the tube. Tube 8 may, in certain preferred embodiments, be a heat shrinkable tube and the tube sealing apparatus may be a device for applying focused heat to each of the seal locations along the length of the tube.

Figure 10:
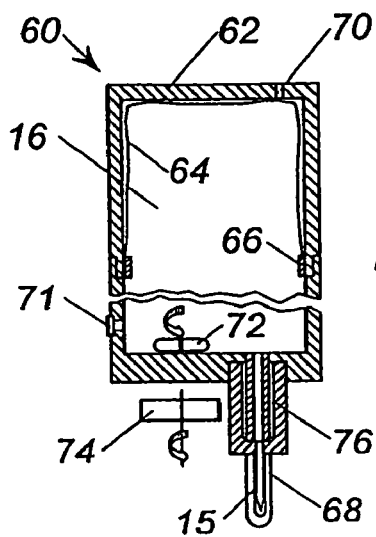
FIG. 10 is a schematic section view of a reagent cartridge suitable for use in the sample testing system of FIG. 1.

In another preferred embodiment, shown in FIG. 10, reagent reservoir 16 may be contained in a reagent cartridge 60 having housing 62. Bladder 64 is disposed within housing 62 and is secured to an inner wall of housing 62 by ring 66. Reagent is thus contained within bladder 64. Needle 15 extends from housing 62 and is preferably covered by resilient cover 68. Vent 70 is provided in an upper surface of housing 62 and a filler plug 71 is provided in housing 62 for adding reagent. In certain preferred embodiments, magnetic stirrer 72 is positioned in reservoir 16 on a bottom surface of housing 62. A magnetic field generator 74 positioned outside housing 62 creates rotation of magnetic stirrer 72, mixing the reagent, e.g. a cell suspension, prior to injection into tubule 14. The reagent may also be mixed by other means such as shaking. Tube 76 of piezoelectric material surrounds needle 15 and serves as a drop generator as described more fully in U.S. Pat. No. 4,329,698, the contents of which are incorporated herein by reference. Multiple reservoirs 16 of reagent may be contained within reagent cartridge 60, allowing different reagents to be added to different tubules 14 as they pass through testing machine 2.

Figure 22:
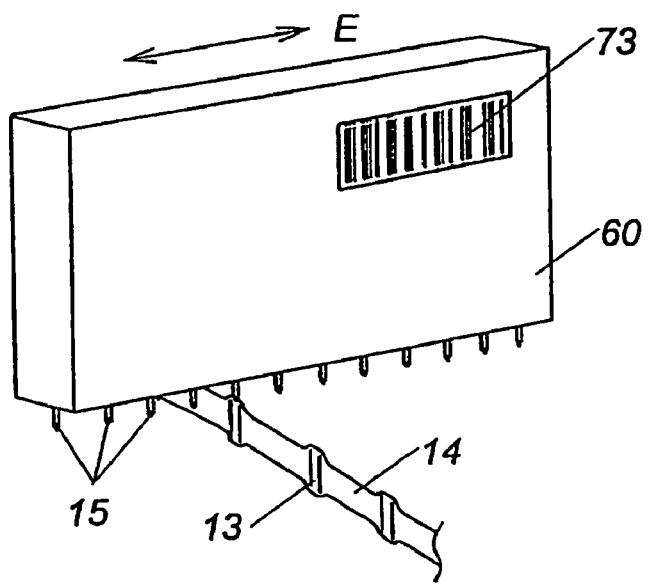
FIG. 22 is a schematic perspective view of a reagent cartridge and a tube divided into tubules, suitable for the sample testing system of FIG. 1.

One preferred embodiment is shown in FIG. 22. In the illustrated embodiment, reagent cartridge 60 contains 12 reservoirs of different reagents, each reservoir having its own needle 15, and each reagent being used for a specific test. A bar code label 73 on reagent cartridge 60 provides information to identify particular reagents contained therein and test procedure necessary for programming the sample test system. Tubules 14 are moved in an axial direction, preferably in step-wise fashion, past reagent cartridge 60. Reagent cartridge 60 is movable in a direction transverse to a longitudinal axis of the tubules in order to position the proper needle 15 corresponding to a desired reagent, at the injection channel of each tubule in turn. Once reagent cartridge 60 is properly positioned, needle 15 is injected into tubule 14 to inject the desired reagent.

Figure 11:
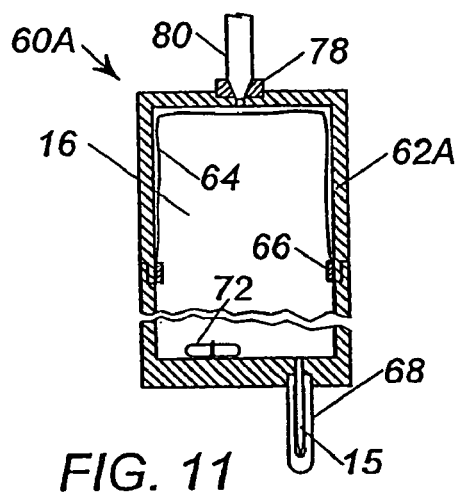
FIG. 11 is a schematic section view of an alternative embodiment of a reagent cartridge for the sample testing system of FIG. 1.
Figure 12:
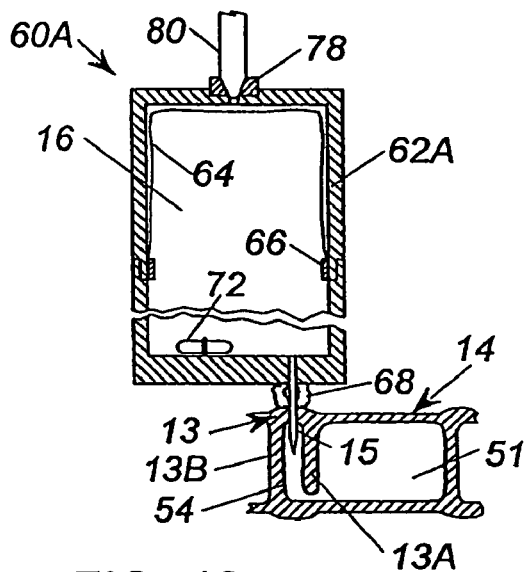
FIG. 12 is a schematic section view of the reagent cartridge of FIG. 11 shown injecting reagent into a tubule.

Another preferred embodiment is shown in FIG. 11, where reagent cartridge 60A has housing 62A with an adapter 78 located on an upper surface of housing 62A to receive air nozzle 80. In use, as seen in FIG. 12, needle 15 extends through resilient cover 68 and penetrates the wall of tubule 14. In the preferred embodiment illustrated, needle 15 extends into injection channel 54. Air pressure is introduced onto bladder 64 through air nozzle 80, causing reagent from reservoir 16 to be forced into tubule 14. In the embodiment illustrated, needle 15 is fixed with respect to reagent cartridge 60A, and the entire reagent cartridge 60A is moved vertically by actuator 49 (seen in FIG. 1) in order to inject needle 15 into tubule 14. In other preferred embodiments, needle 15 may be independent of reagent cartridge 60A such that only needle 15 moves in order to inject reagent into tubule 14.

Figure 13:
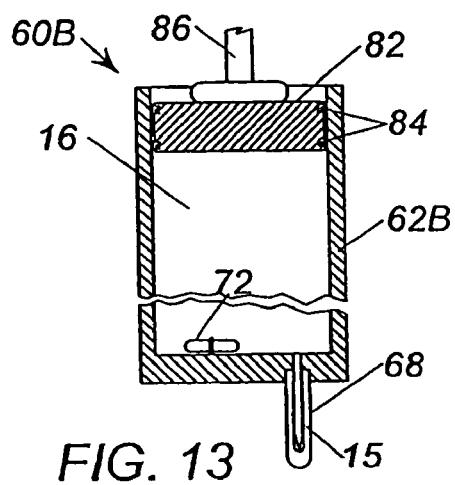
FIG. 13 is a schematic section view of another alternative embodiment of a reagent cartridge of the sample testing system of FIG. 1.

Another preferred embodiment is shown in FIG. 13, where reagent cartridge 60B comprises housing 62B having piston 82 disposed therein above reservoir 16 containing reagent. A pair of resilient annular rings 84 are positioned between piston 82 and an inner wall of housing 62B, providing a seal between piston 82 and housing 62B. Shaft 86 is in contact with the upper surface of piston 82 and pressure is introduced into reservoir 16 as shaft 86 causes piston 82 to be lowered. The pressure in reservoir 16 forces reagent through needle 15 into tubule 14.

Figure 14:
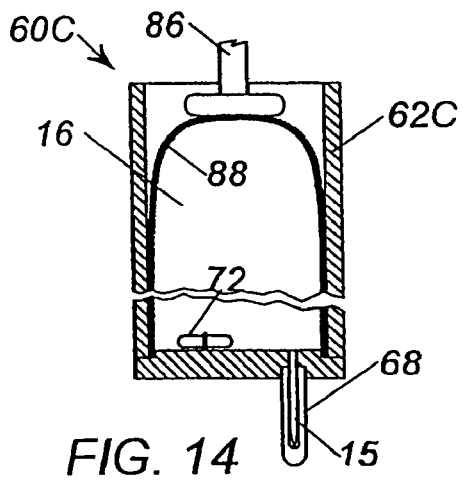
FIG. 14 is a schematic section view of yet another alternative embodiment of a reagent cartridge of the sample testing system of FIG. 1.

Yet another embodiment is shown in FIG. 14, where reagent cartridge 60C comprises housing 62C having resilient sac 88 forming reservoir 16 therein. Shaft 86 engages an outer surface of sac 88, introducing pressure into reservoir 16 in order to force reagent through needle 15.

In other preferred embodiments, multiple reagent cartridges, each having a single reservoir or reagent, may be chained together with a flexible connector such that a large number of reagent cartridges may be connected together. The connected reagent cartridges can then, for example, be rolled up to facilitate storage and delivery.

In certain preferred embodiments, a reagent cartridge with multiple needles in fluid communication with a single, or corresponding multiple reservoirs, may be used to inject, or deposit reagent simultaneously, or sequentially, into multiple different tubules. The reagent cartridge may also be used to inject or deposit reagent into other chambers or containers. For example, a reagent cartridge with multiple needles in fluid communication with a single, or corresponding multiple reservoirs, can be used to simultaneously, or sequentially, inject or deposit reagent into a plurality of containers, such as the recesses of a ninety-six well microplate.

Figure 15:
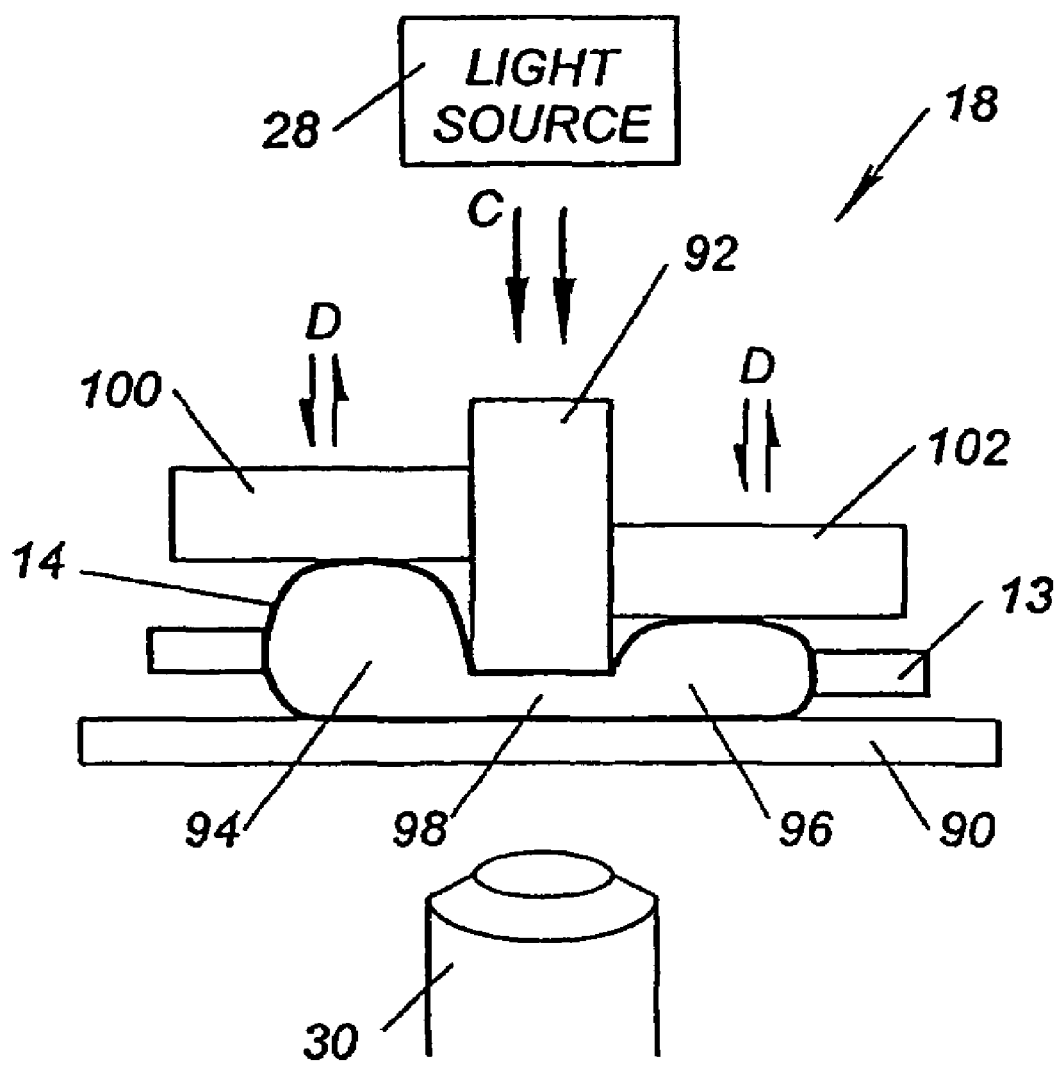
FIG. 15 is a schematic elevation view of a flow control device and inspection system of the sample testing system of FIG. 1.

Flow control device 18 is seen in FIG. 15 and comprises transparent base member 90 upon which tubule 14 is placed. Transparent central plunger 92 is positioned above tubule 14 and lowered onto tubule 14 such that tubule 14 is sandwiched between central plunger 92 and base member 90, creating first and second reservoir zones 94, 96 in tubule 14, with a narrow flow passage 98 extending therebetween through which a thin layer of sample flows. A first outer plunger 100 is positioned above first reservoir zone 94 and a second outer plunger 102 is positioned above second reservoir zone 96. First and second outer plungers or contact members 100, 102 are alternately raised and lowered (shown by arrows D), engaging and disengaging tubule 14, creating a flow of fluid sample 51 back and forth through narrow flow passage 98. By sensing the pressure needed to cause the flow of fluid sample 51 through passage 98, the specific molecular binding strength between cells or particles in the sample can be determined. The number of particles or cells in the sample can be counted, and cell properties such as size and light intensity can be measured. In a preferred embodiment, the height of, or gap created by, flow passage 98 is approximately 10 µm to 100 µm, depending on the assay performed. Through such a narrow passageway, the flow of fluid sample 51 can be analyzed by computerized microscopic inspection system 20. Light from light source 28, shown by arrows C, is projected through central plunger 92 and passage 98. Images of fluid sample 51 as it flows through passage 98 are captured by camera with microscopic lens 30 which then transfers the images through frame grabber 32 to computer 34 (seen in FIG. 2) for analysis through known signal processing algorithms. It is to be appreciated that operation of flow control device 18 may, in certain preferred embodiments, include portions of time where no flow is generated through passage 98, and camera 30 may capture images of fluid sample 51 during these non-flow periods. Camera 30 is, in certain preferred embodiments, a charged-coupled device (CCD) camera. Cell interaction kinetics can be analyzed by computer 34 by monitoring cell motion and/or location as well as optical properties of the cells such as light scattering.

Cell-cell interaction occurs in tubule 14 when any of certain known reagents are added to a blood sample. Molecular interactions occur when the reagent is added to the sample. Aggregates may be formed in the sample, and the size and distribution of the aggregates varies depending on the type of reagent added to fluid sample 51, the shear flow of the sample, and the time period elapsed after injection of the reagent. In a known fashion, the size and quantity of aggregates passing through flow passage 98 allows various types of screening or analysis to be performed on fluid sample 51. For example, immunodiagnosis such as blood typing, antibody screening and infectious disease testing can be performed using the present invention by selecting suitable known reagents to be injected into one or more tubules. Specifically, blood forward typing can be performed by adding a related antibody as the reagent to fluid sample 51 comprising whole blood. Blood reverse typing can be performed by adding a cell suspension as the reagent to fluid sample 51 comprising plasma. Blood reverse typing can also be performed by adding cell suspension as the reagent to fluid sample 51 comprising whole blood. Hematology tests for blood components such as red and white blood cell counts, coagulation and aggregation time testing, and platelet function tests can be performed as well. The reagent may comprise anti-analyte coated beads in order to detect specific analyte in the sample. Other tests such as nucleic acid amplification and DNA analysis may also be performed in the manner disclosed here. Blood chemistry analysis can detect, for example, sugar levels, cholesterol levels, etc. Drug compound testing can also be performed using the present invention. Other testing which can be performed using the present invention will become readily apparent to those skilled in the art, given the benefit of this disclosure.

The present invention provides many advantages. A testing machine can be used cost effectively for many different tests and groups of tests. The testing machine has high throughput and low complexity for ease of operation. Biosafety is increased due to reduced handling of samples such as blood.

Computer 34, in certain preferred embodiments, may be operably connected to tube advancing system 3, tube sealing apparatus 12, flow control device 18, incubation chamber 19, centrifuge 35, and inspection system 20 by cables (not shown). Computer 34 can provide control and coordination of the operating parameters of the components of testing machine 2 in a known fashion, and further description of the control of the components of testing machine 2 need not be provided here.

Figure 16:
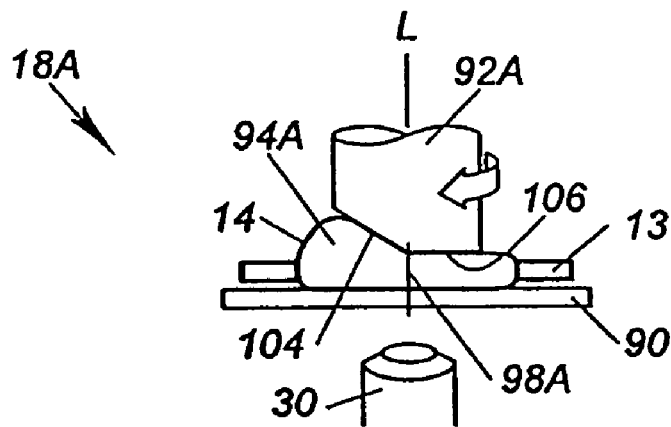
FIG. 16 is a schematic elevation view of an alternative embodiment of the flow control device of the sample testing system of FIG. 1.

In another preferred embodiment, shown in FIG. 16, flow control device 18A comprises transparent cylindrical plunger 92A having a longitudinal axis L and a beveled surface 104 formed on lower surface 106 of plunger 92A. A reservoir 94A is formed beneath beveled surface 104 and passage 98A is formed beneath lower surface 106. As plunger 92A is rotated about longitudinal axis L, flow through passage 98A can be observed in the same manner described above.

Figure 17:
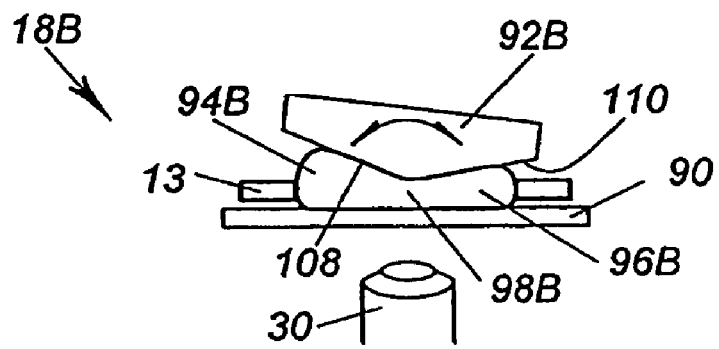
FIG. 17 is a schematic elevation view of another alternative embodiment of the flow control device of the sample testing system of FIG. 1.

Another preferred embodiment is shown in FIG. 17, where flow control device 18B comprises transparent plunger 92B having first and second beveled surfaces 108, 110 formed on a lower surface thereof. First and second reservoirs 94B, 96B are formed beneath beveled surfaces 108, 100, respectively, with narrow passage 98B extending therebetween. As plunger 92B is rocked back and forth, fluid sample 51 passes back and forth from first reservoir 94B to second reservoir 96B through passage 98B. The flow of fluid sample 51 is observed by camera 30 as described above.

Figure 18:
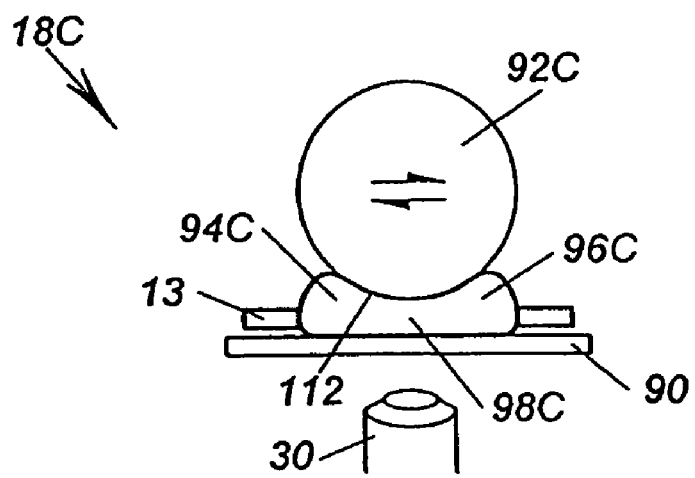
FIG. 18 is a schematic elevation view of yet another alternative embodiment of the flow control device of the sample testing system of FIG. 1.

Yet another embodiment is shown in FIG. 18, where flow control device 18C comprises transparent plunger 92C whose lower surface 112 has an arcuate profile. The arcuate profile of lower surface 112 creates a narrow flow passage 98C extending between a first reservoir 94C and a second reservoir 96C. Plunger 92C is rolled back and forth, forcing fluid sample 51 back and forth from first reservoir 94C to second reservoir 96C through flow passage 98C. The flow of fluid sample 51 through flow passage 98C is observed by camera 30 as described above.

Figure 19:
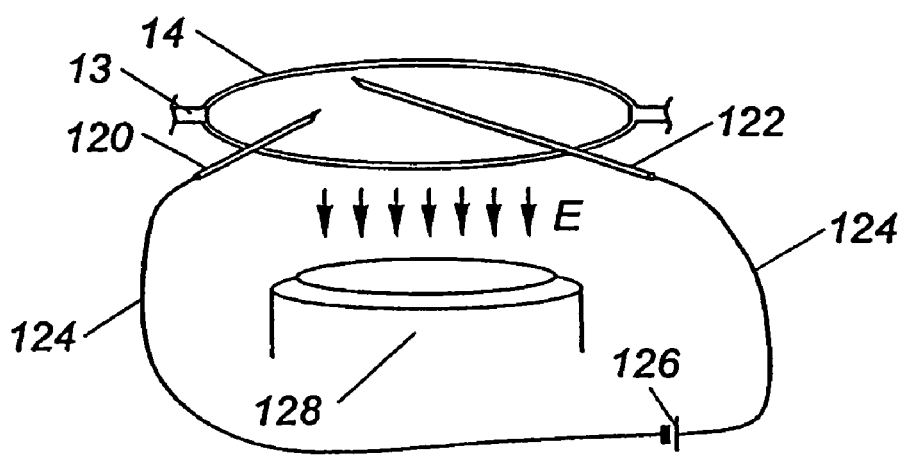
FIG. 19 is a schematic elevation view of an alternative embodiment of the inspection system of the sample testing system of FIG. 1.

In certain preferred embodiments, as seen in FIG. 19, a first electrode 120 and a second electrode 122 are inserted into tubule 14 and are connected by cables 124 to voltage source 126 which creates a voltage difference between first and second electrodes 120, 122. Red blood cells in fluid sample 51 within tubule 14 are negatively charged so that by electrophoresis they are attracted to the positively charged electrode 122. An electrochemiluminescent reagent is added to tubule 14 by reagent cartridge 60 or other suitable means, creating an electrochemiluminescent reaction near the surface of electrode 122 which causes a particular light to be emitted (shown by arrows E) from electrode 122 based on the type of reagent added to tubule 14. Sensor 128 receives the transmitted light and generates a corresponding electrical signal which is sent to computer 34 for analysis, display, recording, etc. In other preferred embodiments, a current is passed by first and second electrodes 120, 122 through the sample. In this embodiment, certain electrochemical properties of the sample can be measured by analyzing the voltage difference between the first and second electrodes 120, 122.

Figure 20:
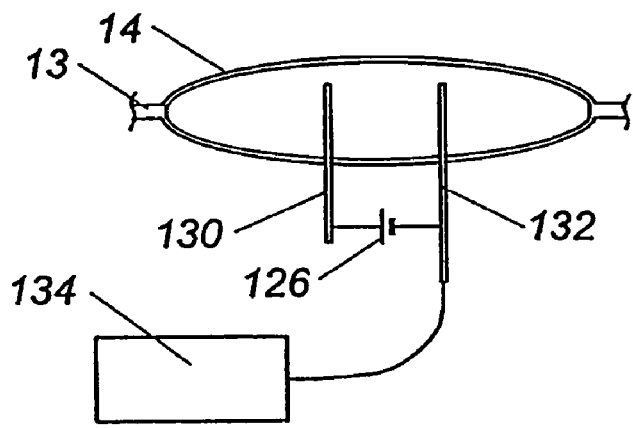
FIG. 20 is a schematic elevation view of another alternative embodiment of the inspection system of the sample testing system of FIG. 1.

Another preferred embodiment is shown in FIG. 20. First and second electrodes 130, 132 are inserted into tubule 14. Second electrode 132 is a fiberoptic sensor. As described above with respect to FIG. 19, an electrochemiluminescent reaction occurs near the surface of electrode 132 causing light to be generated. The light travels through fiberoptic electrode 132 to a fiber optic sensor, or reader 134 which captures and interprets the information provided by the type of light generated. Second electrode 132 preferably has a diameter between approximately 0.4 mm and 1 mm. Second electrode 132 is formed of a material or is coated with a material suitable for providing sufficient conductivity.

Figure 21:
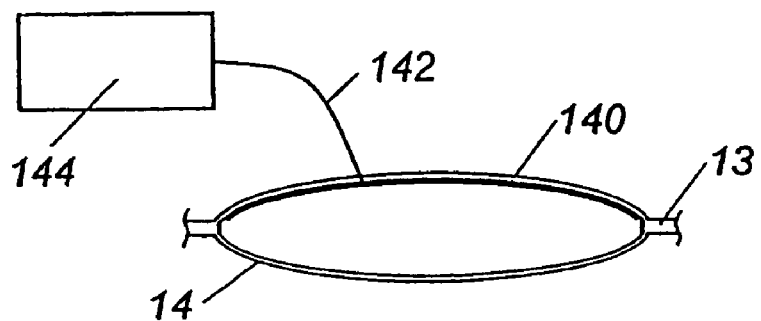
FIG. 21 is a schematic elevation view of a coating being applied to a tubule of the present invention.

In certain preferred embodiments, a coating may be deposited on tubule 14 to increase visibility through the wall of tubule 14. As seen in FIG. 21, a coating material 140 is transferred through conduit 142 from coating supply 144 and deposited on the outer surface of tubule 14. If the walls of tubule 14 are translucent, the addition of coating 140 to the outer surface of tubule 14 can make the walls of tubule 14 substantially transparent, increasing the effectiveness of viewing the flow of fluid sample 51 through flow passage 98. Coating 140 preferably has the same optical refractive index as that of the walls of tubule 14. Suitable materials for coating 140 are dependent on the material of tubule 14 and include, for example, oil.

Figure 23:
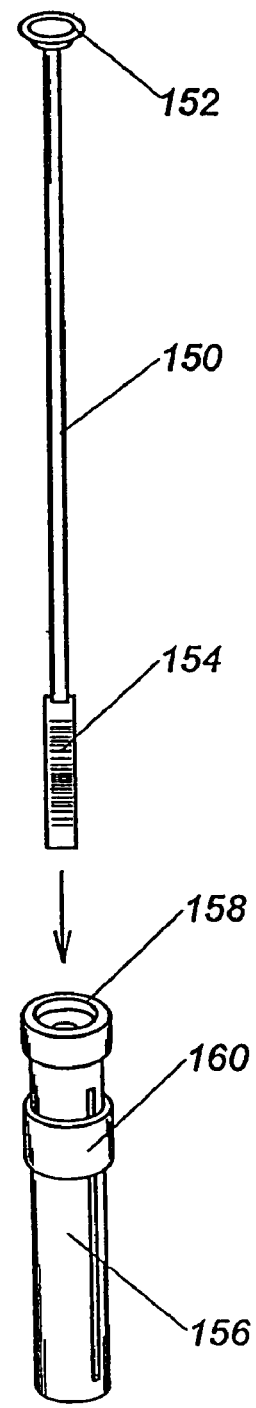
FIG. 23 is a schematic perspective view of one preferred embodiment of a tube of the present invention and a drawing device into which the tube is placed.

Suitable methods for filling a tube with a sample will be apparent to those skilled in the art, given the benefit of this disclosure. Exemplary methods include injecting sample fluid into one end of a tube or drawing sample into a tube by creating a vacuum in the tube. A suitable tube 150 is shown in FIG. 23, having a self-sealing head 152 at a first end thereof for needle penetration. Tube 150 may have a label 154 to assist in identifying the source of the sample, e.g., a patient's name when the sample is blood. Label 154 may be, e.g., a bar code label. Tube 150 is inserted into a tube-like drawing device 156 through an aperture 158 at a first end of drawing device 156. To draw a sample into tube 150, the tube-like drawing device 156 is plugged into a needle holder commonly used for drawing blood into a vacuum tube, and slide handle 160 is moved downwardly along drawing device 156. A pair of opposed rollers (not shown) within drawing device 156 and operably connected to slide handle 160 compress a portion of, and roll downwardly along, tube 150, pumping or drawing a sample of blood into tube 150.

In some cases a multiple stage reaction within a segment of a chamber may be desired. In one embodiment, the reagent is injected through an injection channel in the segment, reacted with the contents therein, and then, later, a second reagent is added and reacted with the contents. In an alternative preferred embodiment, the segment may be formed with a pressure gate, separating the volume of the segment into two compartments between which there is fluid communication only at pressure levels achieved by application of external pressure. Pressure for moving sample material from one compartment into an adjacent compartment may be applied, e.g., by hand or by automatic mechanical pressure devices such as those shown in FIGS. 2, 4, 5 and adapted to apply pressure to a single compartment.

Figure 25:
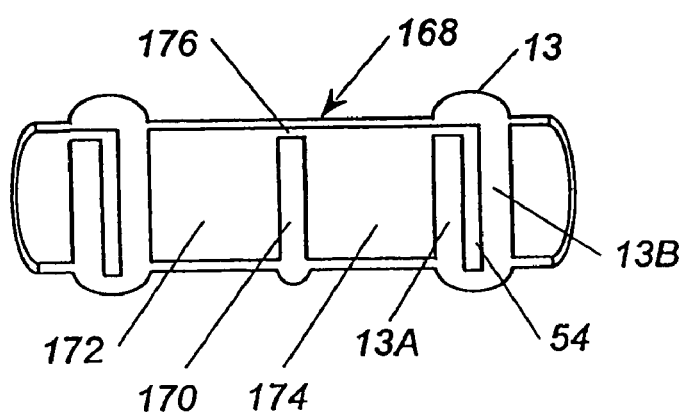
FIG. 25 is a schematic plan view of an alternative embodiment of a tubule of the present invention, shown with a pressure gate between compartments of the tubule.

One preferred example is shown in FIG. 25, where a segment or tubule 168 is separated by a seal 170 into first compartment 172 and second compartment 174. Seal 170 is formed in a manner as described above with respect to seal 13. Seal 170 forms a pressure gate 176, which, under normal operating conditions, provides a fluid-tight seal between first and second sub-segments or compartments 172, 174. In a preferred embodiment, pressure gate 176 opens upon application of pressure greater than a certain value, for example, approximately 2 atm. When external pressure is applied to one of the compartments, pressure gate 176 opens, allowing fluid to flow from the high pressure compartment to the low pressure compartment. One preferred application is in a two stage antibody screening wherein first compartment 172 of tubule 168 is pre-filled with plasma. A first reagent is injected through injection channel 54 into second compartment 174. External pressure is then applied to second compartment 174, forcing the first reagent into first compartment 172. A second reagent is added to second compartment 174 through injection channel 54. Tubule 168 is then conveyed by suitable means to incubation chamber 19 for a predetermined time period of incubation. Tubule 168 is then conveyed by suitable means to centrifuge 35 where tubule 168 is spun such that the cells of the first reagent accumulate proximate pressure gate 176. In certain preferred embodiments, the second reagent may be added after tubule 168 has been incubated in incubation chamber 19 or spun in centrifuge 35. External pressure is applied to first compartment 172 such that cells of the first reagent are passed to second compartment 174. Tubule 168 is then conveyed to flow control device 18 and inspected by inspection system 20 in the manner described above.

In light of the foregoing disclosure of the invention and description of the preferred embodiments, those skilled in this area of technology will readily understand that various modifications and adaptations can be made without departing from the true scope and spirit of the invention. All such modifications and adaptations are intended to be covered by the following claims.

The invention claimed is:

1. A sample testing system, comprising:
   a housing;
   a cavity in the housing, so sized and shaped to receive a chamber;
   a first contact member, so positioned:
   as to be engageable with a first flexible segment of the chamber when the chamber is in the cavity; and
   as to compress the first flexible segment, thereby driving fluid flow from the first flexible segment through a central segment of the chamber to a second flexible segment of the chamber;
   a second contact member so positioned:
   as to be engageable with the second flexible segment of the chamber when the chamber is in the cavity; and
   as to compress the second flexible segment, thereby driving fluid flow from the second flexible segment through the central segment to the first flexible segment; and
   a sensor to sense a condition of a fluid sample in the chamber and to generate an output signal indicative of that condition.

2. The sample testing system of claim 1, wherein the central segment defines a gap to control a thickness of a fluid layer in the central segment of the chamber.

3. The sample testing system of claim 1, wherein the first segment, the central segment, and the second segment of the chamber are arranged to be substantially linear.

4. The sample testing system of claim 1, further comprising a third contact member so positioned:
   as to be engageable with the central segment of the chamber when the chamber is in the cavity; and
   as to compress the central segment, thereby defining a gap of the central segment of the chamber.

5. The sample testing system of claim 1, further comprising a base member so positioned as to support the chamber when the chamber is in the cavity, at least of the contact members being so movable toward the base member as to compress the respective segment of the chamber against the base member.

6. The sample testing system of claim 5, wherein at least a portion of the base member is transparent.

7. The sample testing system of claim 1, wherein at least a portion of at least one contact member is transparent.

8. The sample testing system of claim 1, further comprising a light source so positioned as to project light through a wall of the chamber.

9. The sample testing system of claim 8, wherein the light source projects light through a first wall of the chamber, and the sensor detects light through a second wall of the chamber.

10. The sample testing system of claim 1, wherein the sensor comprises a light detector so positioned as to receive light emanating from the fluid sample through a wall of the chamber, the output signal being in response to the light received.

11. The sample testing system of claim 1, wherein the sensor is so positioned as to sense a condition of a fluid sample located in the central segment, the output signal being indicative of the condition of the fluid sample located in the central segment.

12. The sample testing system of claim 1, further comprising a temperature control device to control the temperature of at least one segment of the chamber.

13. A sample testing system, comprising:
   a housing;
   a cavity in the housing, so sized and shaped to receive a chamber;
   a first contact member, so positioned:

as to be engageable with a first segment of the chamber when the chamber is in the cavity; and as to compress the first segment, thereby defining a gap of the first segment of the chamber and a reservoir in at least a second segment of the chamber;

a second contact member, so positioned:

as to be engageable with a segment of the chamber when the chamber is in the cavity; and as to compress that segment, thereby driving fluid flow from the reservoir in the second segment to the first segment of the chamber; and a sensor to sense a condition of a fluid sample in the chamber and to generate an output signal indicative of that condition.

14. The sample testing system of claim 13, further comprising a base member so positioned as to support the chamber when the chamber is in the cavity, the at least one contact member being so movable towards the base member as to compress at least one portion of the chamber against the base member.

15. A sample testing system, comprising:

a housing;

a cavity in the housing, so sized and shaped to receive a chamber;

at least one contact member, so positioned:

as to be engageable with a first segment of the chamber when the chamber is in the cavity; and as to compress the first segment, thereby defining a gap of the first segment of the chamber and a reservoir in at least a second segment of the chamber;

a base member so positioned as to support the chamber when the chamber is in the cavity, the at least one contact member being so movable towards the base member as to compress at least one portion of the chamber against the base member; and a sensor to sense a condition of a fluid sample in the chamber and to generate an output signal indicative of that condition.

16. The sample testing system of claim 15, wherein at least a portion of the base member is transparent.

17. The sample testing system of claim 15, wherein the at least one contact member has a substantially convex profile to impress a corresponding segment profile.

18. The sample testing system of claim 15, wherein at least a portion of the at least one contact member is transparent.

19. The sample testing system of claim 15, further comprising a light source so positioned as to project light through a wall of the chamber.

20. The sample testing system of claim 19, wherein the light source projects light through a first wall of the chamber, and the sensor detects light through a second wall of the chamber.

21. The sample testing system of claim 15, wherein the sensor comprises a light detector so positioned as to receive light emanating from the fluid sample through a wall of the chamber, the output signal being in response to the light received.

22. The sample testing system of claim 15, further comprising a temperature control device to control the temperature of at least one segment of the chamber.

* * * * *

UNITED STATES PATENT AND TRADEMARK OFFICE
CERTIFICATE OF CORRECTION

PATENT NO. : 7,337,072 B2  Page 1 of 1
APPLICATION NO. : 10/863603
DATED : February 26, 2008
INVENTOR(S) : Shuqi Chen It is certified that error appears in the above-identified patent and that said Letters Patent is hereby corrected as shown below:

Column 14, Ln 34,
Claim 5, insert --one-- after "at least."

Column 15, Ln 17,
Claim 14, delete "the" from before "at least one contact member"

Signed and Sealed this

Sixteenth Day of December, 2008

JON W. DUDAS
*Director of the United States Patent and Trademark Office*